(12) United States Patent
Kuhn

(10) Patent No.: US 7,325,778 B2
(45) Date of Patent: Feb. 5, 2008

(54) CATCHING DEVICE FOR A SUSPENSION SYSTEM

(75) Inventor: Peter Kuhn, Munich (DE)

(73) Assignee: MAVID GmbH, Munich (DE)

( * ) Notice: Subject to any disclaimer, the term of this patent is extended or adjusted under 35 U.S.C. 154(b) by 158 days.

(21) Appl. No.: 10/399,650

(22) PCT Filed: Apr. 11, 2001

(86) PCT No.: PCT/EP01/04164

§ 371 (c)(1),
(2), (4) Date: Aug. 14, 2003

(87) PCT Pub. No.: WO02/33307

PCT Pub. Date: Apr. 25, 2002

(65) Prior Publication Data

US 2004/0245424 A1    Dec. 9, 2004

(30) Foreign Application Priority Data

Oct. 19, 2000    (DE) ............................. 100 51 898

(51) Int. Cl.
*A47H 1/10* (2006.01)
(52) U.S. Cl. .................. 248/327; 248/328; 248/317
(58) Field of Classification Search ........... 248/328, 248/329, 327, 317, 340, 322, 320, 489, 493, 248/58

See application file for complete search history.

(56) References Cited

U.S. PATENT DOCUMENTS

| | | | |
|---|---|---|---|
| 598,164 A * | 2/1898 | Southington | 245/435 |
| 4,724,797 A * | 2/1988 | Steudler, Jr. | 119/72 |
| 4,738,444 A * | 4/1988 | Linden | 482/24 |
| 4,934,001 A * | 6/1990 | Landreth | 4/615 |
| 5,937,073 A | 8/1999 | Van Gieson | |

FOREIGN PATENT DOCUMENTS

DE    298 18 108 U1    3/1999
GB    2 200 491 A    8/1988

* cited by examiner

*Primary Examiner*—Kimberly T. Wood
(74) *Attorney, Agent, or Firm*—Scully, Scott, Murphy & Presser, P.C.

(57) ABSTRACT

A fastening device (1) for attaching utensils hanging on a suspension system in such a way that they do not fall off. The device includes a fastening loop (5) which can be looped around a rod (3) pertaining to the suspension system in order to be connected to the suspension system. The fastening loop (5) is wider (22) at the ends thereof (21), the widened ends penetrating openings (19) formed in a retaining body (6). The fastening device (1) also includes a main body (9) which can be connected to a fastening rod (17) of a connection element (10) by a fastening pin (12), with the connection element being fixed to the utensils.

8 Claims, 3 Drawing Sheets

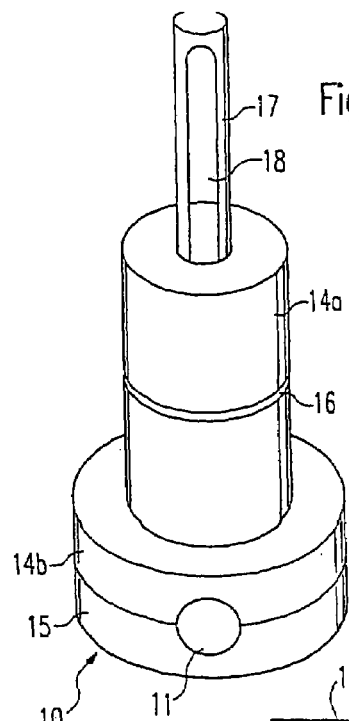
Fig. 2B
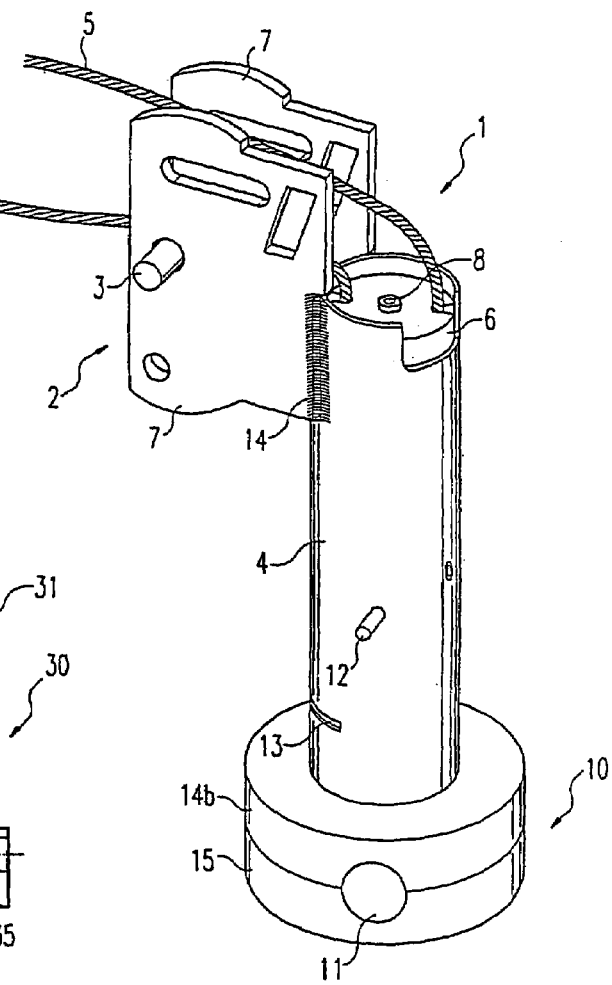
Fig. 1
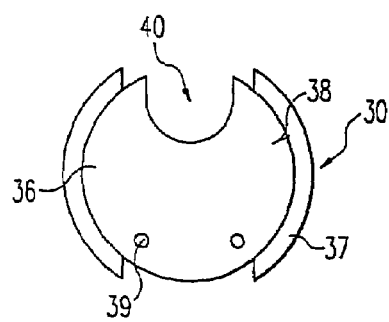
Fig. 6A
Fig. 6B

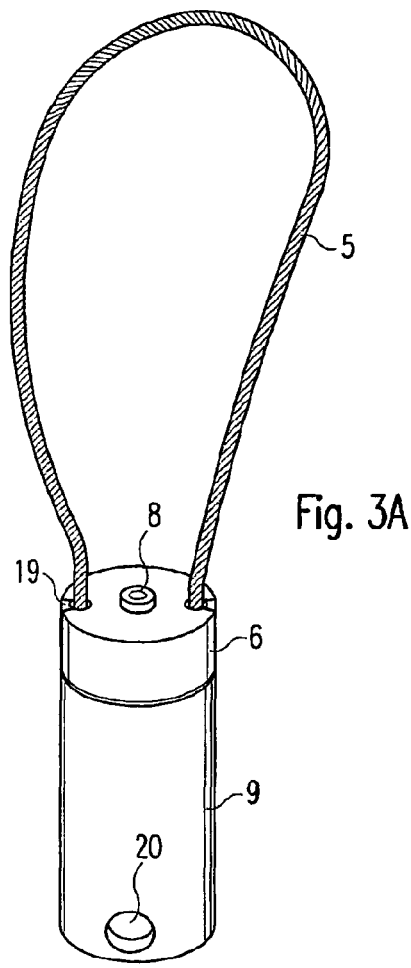
Fig. 3A
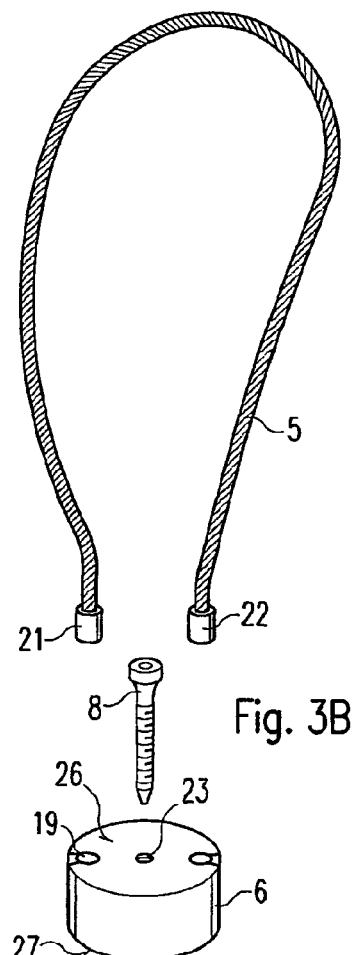
Fig. 3B
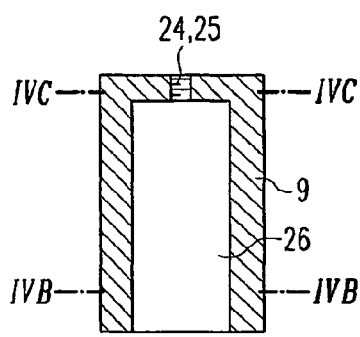
Fig. 4A
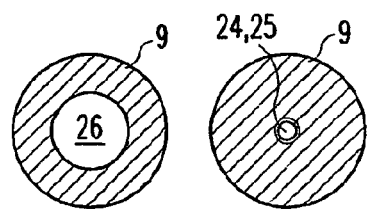
Fig. 4B  Fig. 4C
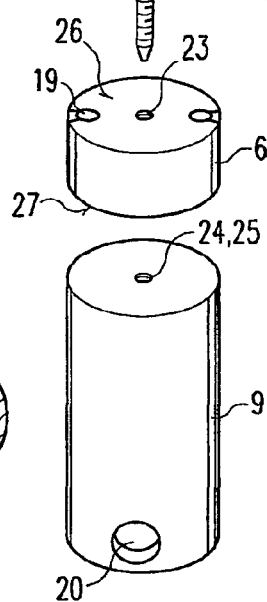
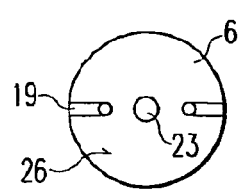
Fig. 5A
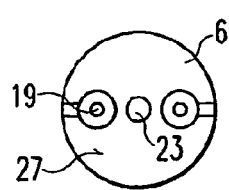
Fig. 5B
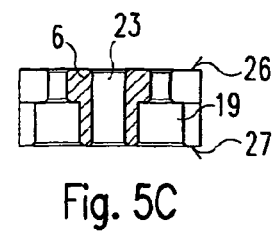
Fig. 5C

CATCHING DEVICE FOR A SUSPENSION SYSTEM

The invention relates to a catching device for securing a suspension apparatus.

Suspension apparatuses of the present kind serve to keep utensils in readiness in suspended working positions in the area of working places. Preferred uses for a present suspension apparatus are medical treatment areas in doctors' practices and hospitals and medical technicians' work spaces in medical laboratories. Utensils which can be provided by a suspension apparatus, can be, e.g. X-ray screens, measuring equipment, picture reproduction equipment (monitors), stored parts for working and treatment tools and suchlike.

Owing to the sometimes great weight of the utensils provided by means of the suspension apparatus and the frequent adjustment of position and height of the extension arms of the suspension apparatus, which are usually long and of multiple parts, fatigue phenomena and subsequently breaks at weak points can arise. This includes in particular hinge joints and suspension points. In order to prevent accidents and injuries to the group of staff located in the area of the suspension apparatus, it must therefore be ensured that the suspension apparatus is secured in the event of breaks in such a way that the parts breaking off cannot fall to the floor.

A device known from DE 298 18 108 U1 for fastening a suspension apparatus to a carrier comprises a securing element, which is additionally anchored to the main fastening of the suspension apparatus, for example to a carrier or the ceiling of a room. The securing element is therein fixed by a first end to the suspension apparatus and by a second end to the carrier or the ceiling of the room. It can be constructed in the form of a belt, chain or rope or else consist of a telescopic rod.

Furthermore, from U.S. Pat. No. 5,937,073 a securing device for a mounting for a loudspeaker, attached for example by suspension to the ceiling of a room, is known, wherein the loudspeaker is connected to the mounting by a rope or cable and a spring hook and is therefore secured against falling.

The object of the invention is, by means of a simply constructed and easily mounted catching device, to increase the operational safety of a suspension apparatus and simultaneously to prevent damage to the utensils provided by the suspension apparatus.

This object is achieved by the features of claim 1.

In the catching device according to the invention a restraining part has a security loop which can be placed into a securing body of the catching device, designed in one or more parts. The security loop is configured in such a way that it can be looped round a bolt, or similar, either in the joint of the suspension apparatus located closest to the catching device or in the further course of the carrying arm, thus securing a utensil connected to the main part of the catching device and suspended on the suspension apparatus in a simple manner against falling.

Advantageously not only is the utensil connected to the catching device but the catching device is also connected to the suspension apparatus. Simultaneously all three parts are connected via a securing pin which is pushed through the main part of the catching device, so the catching device secures the broken off parts both in the event of fatigue breaks of the suspension apparatus and in the event of a malfunction or a break in the connecting element of the utensil.

The catching device is produced in a simple manner and can either be implemented in new equipment during manufacture or retrofitted in already installed suspension apparatuses.

The subordinate claims contain features which further improve the aspired to safety, lead to simple and safe fastening measures, enable a simple form which can be produced at reasonable cost and also guarantee easy and quick assembly.

The invention and further advantages achievable by it are described in greater detail below using preferred embodiment examples and drawings.

FIG. 1 shows a catching device according to the invention mounted in a joint of a suspension apparatus in a perspective overall illustration.

FIG. 2B shows a perspective illustration of a connecting element for attaching a utensil, which element can be combined with the catching device according to the invention.

FIG. 3A shows a perspective illustration of the first embodiment example of the catching device according to the invention.

FIG. 3B shows a perspective illustration of the individual components of the first embodiment example of the catching device according to the invention illustrated in FIG. 3A.

FIGS. 4A to 4C show sections in different planes through a first part of the catching device according to the invention.

FIGS. 5A to 5C show sections in different planes through a second part of the catching device according to the invention.

FIGS. 6A and 6B show two views of a second embodiment example of a catching device configured according to the invention.

FIG. 1 shows in a perspective illustration a first embodiment example of a catching device 1 configured according to the invention in the assembled position in a suspension apparatus as an example.

Figure 2A:
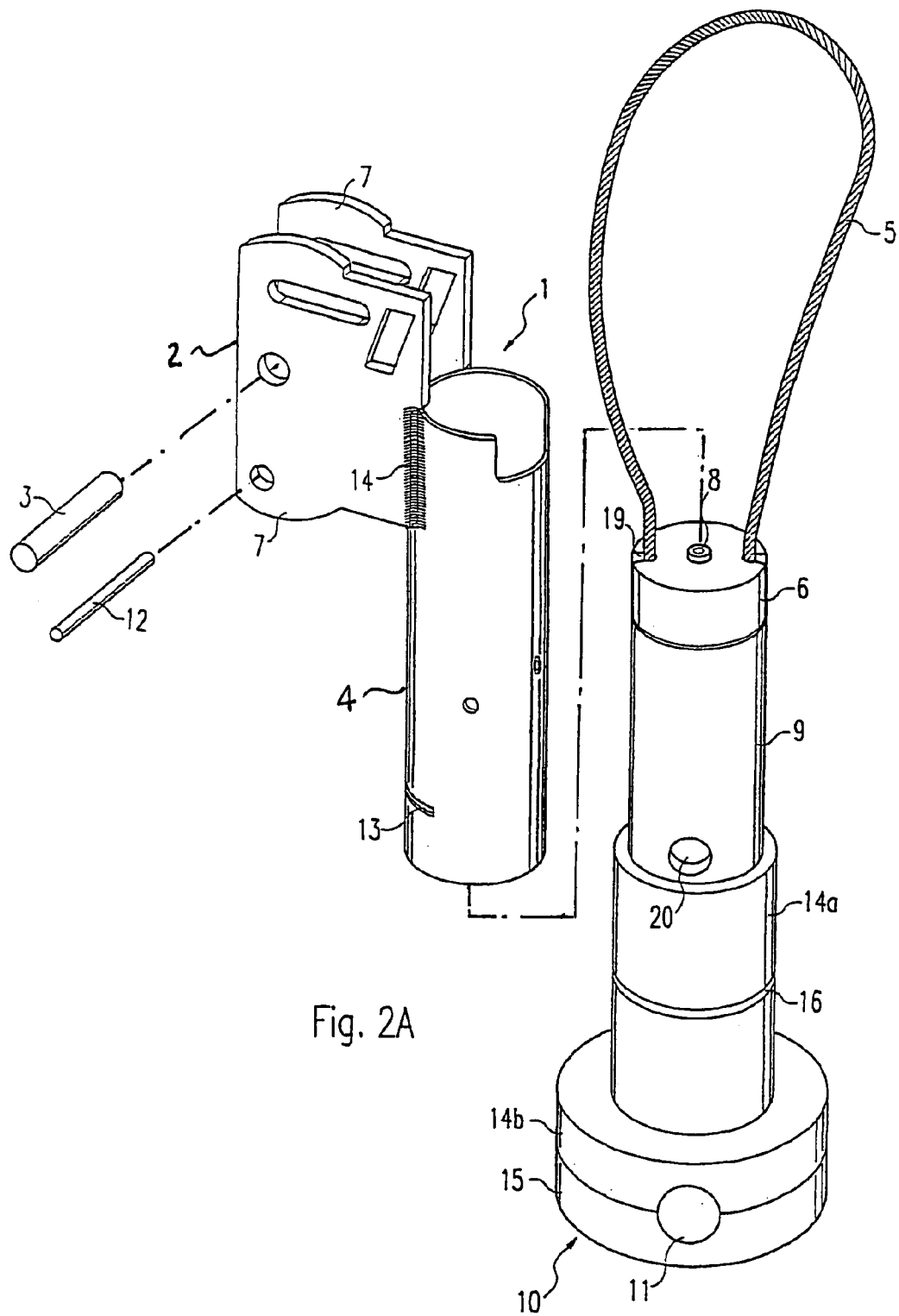
FIG. 2A shows a perspective illustration of the partially dismantled joint with a first embodiment example of the catching device according to the invention.

The suspension apparatus is therein not further illustrated and is represented in the drawings by a bearing journal receiver 2. The bearing journal receiver 2 is attached, for example, on the end of a one- or multiple-part carrying arm of the suspension apparatus and forms a joint by means of a multiple-part bolt connection. A bolt 3 is depicted representationally in FIG. 1.

The catching device 1 is inserted in a receiver sleeve 4 of the bearing journal receiver 2. A security loop 5, connected to a restraining body 6, is arranged between cheeks 7 of the bearing journal receiver 2 in such a way that it forms a curve round the bolt 3. The security loop 5 can therein be dimensioned in such a way that it loops only round the bolt 3, but it can also be long enough for it to extend, for example, partially or completely along the carrying arm and be guided round a bolt or similar in the area of another joint connection. A more precise description of the catching device can be seen in FIGS. 3 to 5.

The restraining part 6 in the first embodiment example is detachably connected to a part 9 of the catching device 1 by a screw 8, i.e. in this embodiment example restraining part 6 and main part 9 are constructed in two parts.

The receiver sleeve 4 in the fully assembled state is pushed over a connecting element 10, which in a recess 11, can receive, for example, a holding rod, not further illustrated, of an X-ray screen or some other utensil. The connecting element 10 is illustrated in greater detail in FIG. 2B.

A securing pin 12, which is pushed through the receiver sleeve 4, the connecting element 10 and the main part 9 of the catching device 1, connects said components to one another. A slit 13, made in the receiver sleeve 4, can accommodate a further securing device, which will not be gone into further here.

By the described arrangement of the catching device 1 configured according to the invention it can therefore be ensured that neither a break in a welding seam 14 connecting the cheeks 7 to the receiver sleeve 4 nor a tear in the receiver sleeve 4 at a weak point, for example in the area of the slit 13, leads to a utensil suspended on the suspension apparatus falling down. The fall is intercepted by the security loop 5 looped round the bolt 3, wherein the fall path is, e.g., only approximately 0.1 m. This can have the additional effect that the break in the receiver sleeve 4 does not go unnoticed, as, for example, would be the case with a security loop 5 placed rigidly round the bolt 3, and repair is arranged.

FIGS. 2A and 2B show in a perspective illustration the partially dismantled arrangement from FIG. 1. Coinciding components are provided with coinciding reference numerals.

In FIG. 2A the pin 12 and the bolt 3 have for this purpose been removed and the receiver sleeve 4 pulled away. The catching device 1 sits on top of the connecting element 10, which, as illustrated in FIG. 2B, consists of a first part 14a, 14b constructed in one piece and formed cylindrically in a step shape with the part 14b being larger in diameter than part 14a, and a second part 15, also formed as cylindrical or disc-shaped. Between the first part 14 and the second part 15 is constructed the recess 11, which, for example, receives the cross rod of an X-ray screen. A groove 16 constructed in the first part 14a corresponds to the above-mentioned additional safety device, not described in greater detail.

The first part 14a of the connecting element 10 has a securing bolt 17, which is guided I the hollow-cylindrical first part 14a and projects out of it. In the securing bolt 17 an elongated hole 18 is constructed, which in the assembled state of the suspension apparatus is penetrated by the pin 12. In the assembled state the main part 9 of the catching device 1, also hollow-cylindrical, is placed on the safety bolt 17 of the connecting element 10.

FIG. 3A shows in a perspective illustration the catching device 1 according to the invention without the other components.

As already mentioned above, the main part 9 of the catching device is constructed as a hollow cylinder. It is connected by a screw 8 or a similar fastening object to the restraining part 6, which in turn fixes the security loop 5. The security loop 5 is therein guided through slit holes 19 in the restraining part 6. A hole 20 in the main part 9 of the catching device 1 serves to lock it by means of the securing pin 12 to the remaining components.

FIG. 3B shows in a perspective illustration the individual components of the catching device 1.

The security loop 5 consists of a rope, a belt, a chain or similar and in the present first embodiment example is designed as a steel rope. This has the advantage of high resistance to breaking, great flexibility and a small diameter. The security loop 5 therein has on each of its ends 21a widened part 22, both of which consist, for example, of sleeves which are placed on and then compressed. The ends 21 of the security loop 5 with the widened parts 22 are then placed in the slit holes 19 of the restraining part 6 and grip underneath them owing to the special shape of the slit holes 19.

As well as the slit holes 19 for the security loop 5, the restraining part 6 has a hole 23 which can be provided as flat or with a thread and is penetrated by the screw 8. The hole 23 corresponds to a hole 24 in the main body 9, provided with a thread 25 fitting the screw 8, so the main part 9 and the restraining part 6 in this embodiment example can be detachably connected.

For assembling the catching device 1 first the security loop 5 is placed round the bolt 3, then the widened parts 22 of the ends 21 of the security loop 5 are placed into the slit holes 19 and finally, by screwing in the screw 8, the restraining part 6 is connected to the main part 9. After this the catching device can be inserted into the receiver sleeve 4, placed on the securing bolt 17 of the connecting element 10 and connected to said components by the securing pin 12.

FIGS. 4A to 4C shown for clarification three schematic sections through the main part 9 of the catching device 1 according to the invention. The first section illustrated in FIG. 4A therein runs in the axial direction.

The main part 9 of the catching device 1 is designed as a hollow cylinder and has a recess 26. The recess 26 continues in the hole 24 with the thread 25. Owing to the simple form of the main part 9 of the catching device 1 simple and reasonably priced manufacture, for example by turning, is possible.

FIG. 4B shows a section along line IVB-IVB in FIG. 4A and FIG. 4C a section along line IVC-IVC. Both sections again clarify the simple form of the main part 9, which is not confined to round cross-sections. Elliptical or multi-sided cross-sections are equally conceivable.

FIGS. 5A to 5C illustrate various views and also a longitudinal section through the restraining part 6. FIG. 5A therein shows an aspect on to a front face 26 facing away from the main part 9, FIG. 5B an aspect on to a front face 27 facing the main part 9 and FIG. 5C a section along the slit holes 19 through the restraining part 6.

As can be seen from FIGS. 5A and 5B, the slit holes 19 extending through the restraining part 6 are variable in diameter. The slit holes 19 are therein shaped in such a way that the widened parts 22 on the ends 21 of the security loop 5 simultaneously penetrate the restraining part 6 and grip it underneath, so they are firmly locked in the axial direction and accordingly fulfil their securing function, while for assembly they can be removed from the slit holes 19 in the radial direction. The widened parts 22 are therein advantageously dimensioned in such a way that they occlude flush without projecting with the front face 27 facing the main part 9.

FIG. 5C again clarifies the two-part shape of the slit holes 19, the diameters of which become smaller from the front face 27 facing the main part 9 to the opposite front face 26 of the restraining part 6 in a step shape and thus enable locking of the security loop 5 in the restraining part 6 which has great tensile strength but is mechanically simple.

FIGS. 6A and 6B show two views of a second embodiment example of a catching device 1 configured according to the invention, in which the main part 9 and the restraining part 6 are constructed in one piece with one another. The overall component is designated below by the term securing body 30.

In contrast to the above-described first embodiment example of a catching device 1 configured according to the invention, the second embodiment example illustrated below has a one-part securing body 30, on which a circulating radial groove 31 is constructed.

The security loop 5 already described above can in the same way as in the previous embodiment example be designed as a chain, belt or wire loop 5. It has on its ends 21 widened parts 22, which consist, for example, of sleeves which have been placed on and then squeezed.

FIG. 6A shows a lateral view of the one-part securing body 30. The circumferential radial groove 31 has orifices 19, into which the security loop 5, not illustrated in FIG. 6A, can be locked.

The securing body 30 has a U-shaped recess 34 for receiving the securing bolt 17 of the connecting element 10. A bezel 35 constructed on the inside of the recess 34 is additionally provided for better adaptation to the shape of the connecting element 10.

The securing body 30 is designed in two steps, wherein in a first step 36 the circulating groove 31 and in a second step 37, the diameter of which exceeds the diameter of the first step 36, the hole 20 is constructed, which serves for locking by the securing pin 12, not further illustrated in FIG. 6A, to the other components.

FIG. 6B shows an aspect from above on to the securing body 30 of the catching device 1 configured according to the invention. The widened part of the second step 37, which has a larger diameter than the first step 36, can be clearly seen.

In a front face 38 of the first step 36 holes 39 are provided, which are arranged in such a way that securing pins, not illustrated here, nailed into the holes 39, fix the position of the widened parts 22 of the ends 21 of the security loop 5 and prevent them from slipping out of the circumferential groove 31.

Furthermore, an axial recess 40 is provided, which extends on the edge through the first step 36 and the second step 37 of the securing body 30. The axial recess 40 is particularly suitable for receiving a cable which serves as electrical supply to the utensil arranged on the suspension apparatus.

For re-securing the suspended utensil the security loop 5, as already described above, is placed round the bolt 3 of the bearing journal receiver 2 of the suspension apparatus and with its ends 21 placed into the radial circumferential groove 31 of the securing body 30. The widened parts 22 of the ends 21 therein lock into the orifices 19 of the securing body 30. Then securing pins are nailed into the holes 39 and positioned in such a way that the widened parts 22 of the ends 21 of the security loop 5 are fixed as stationary in the orifices 19 of the circumferential groove 31 of the securing body 30.

The radially arranged security loop 5 makes space-saving re-securing possible, which is loaded only in the circumferential direction and thus guarantees a high degree of safety.

The invention claimed is:

1. A catching device (1), engaged with a suspension apparatus suspending a utensil from said suspension apparatus so as to secure said utensil from falling, said catching device including a security loop (5), extended about a bolt (3) in the suspension apparatus for forming a connection between the catching device and the suspension apparatus, said security loop (5) having widened parts (22) on opposite free ends (21) thereof, a restraining part (6) of said catching device (1) having orifices (19) formed therein for receiving, respectively, the widened parts (22) of said loop, said catching device (1) further including a main part (9) which includes a pin (12) attaching a securing bolt (17) of a connecting element (10) which has a utensil connected therewith, said orifices (19) in the restraining part (6) each having a diameter which becomes smaller in a step shape extending from a front face (27) of the restraining part (6) facing the main part (9) to a front face (26) located opposite thereto, said orifices latchingly retaining the widened parts (22) of said loop (5) upon said catching device (10) being engaged with said suspension apparatus, and said main part (9) being connected to said restraining part (6) so as to facilitate the secure suspension of the utensil from the suspension apparatus.

2. A catching device according to claim 1, wherein the main part (9) of said catching device is constructed as a hollow cylinder, and said restraining part (6) is a disc member coaxially located at one end of said main part (9).

3. A catching device according to claim 2, wherein a screw (8) fastens the main part (9) to the restraining part (6), said screw (8) extending into a screw hole (25) formed in the main part (9).

4. A catching device according to claim 1, wherein the orifices (19) in said restraining part (6) extend in axial direction of the restraining part (6).

5. A catching device according to claim 1, wherein the security loop (5) is constructed selectively in the form of a belt loop, a chain loop or a wire loop.

6. A catching device according to claim 1, wherein the widened parts (22) on the ends (21) of the security loop (5) are squeezing sleeves fastened to said ends (21).

7. A catching device according to claim 1, wherein the widened parts (22) are lockable into the orifices (19) of the restraining part (6) upon insertion of said restraining part (6) into a receiver sleeve (4) of said suspension apparatus.

8. A catching device according to claim 1, wherein the main part (9) and the restraining part (6) are constructed in one piece to form a securing body (30).

* * * * *